United States Patent [19]

Schlager

[11] 3,996,279
[45] Dec. 7, 1976

[54] NOVEL 2-AMINO METHYL-4,6-DIHALOGENPHENOL DERIVATIVES AND METHODS FOR THE PREPARATION THEREOF

[75] Inventor: Ludwig H. Schlager, Vienna, Austria

[73] Assignee: Gerot-Pharmazeutika Dr. Walter Otto K.G., Vienna, Austria

[22] Filed: Oct. 31, 1974

[21] Appl. No.: 519,710

Related U.S. Application Data

[63] Continuation-in-part of Ser. No. 429,984, Jan. 2, 1974.

[30] Foreign Application Priority Data

| Jan. 2, 1973 | Austria | 1/73 |
| Aug. 24, 1973 | Austria | 7387/73 |
| June 10, 1974 | Denmark | 3097/74 |

[52] U.S. Cl. .................... 260/559 R; 260/247.2 A; 260/247.7 R; 260/268 C; 260/293.76; 260/559 B; 260/559 H

[51] Int. Cl.$^2$ ........................ C07C 103/32

[58] Field of Search ........ 260/559 R, 559 H, 559 B, 260/570.9

[56] References Cited

UNITED STATES PATENTS 3,809,721  5/1974  Schultz et al. ................ 260/570.9

FOREIGN PATENTS OR APPLICATIONS 2,119,066  8/1972  France
2,119,067  8/1972  France

OTHER PUBLICATIONS

Noller, Chem. of Org. Compds., 3rd Ed., W. B. Sanders, Co., (1965), p. 552.

*Primary Examiner*—C. Davis
*Attorney, Agent, or Firm*—Sughrue, Rothwell, Mion, Zinn and Macpeak

[57] ABSTRACT

2-aminomethyl-4,6-dihalogenphenol derivatives and salts thereof with physiologically acceptable acids or bases having the formula:

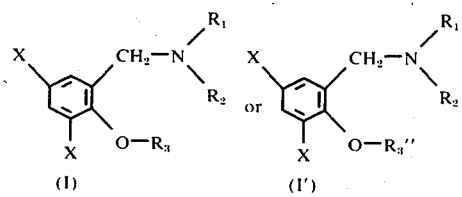

wherein X is the same halogen in both positions, $R_1$ is a hydrogen atom or a lower alkyl group, $R_2$ is an alkyl, cycloalkyl, aryl or aralkyl group, or $R_1$ and $R_2$ together with the nitrogen atom may form a saturated heterocyclic ring, which ring may be interrupted by an oxygen, nitrogen or sulfur atom, $R_3$ is a hydrogen atom, an alkyl, alkoxyalkyl, carboxyalkyl, carbamylalkyl, aralkyl, acyl or sulfonyl group or a base radical, e.g. an alkali metal atom, and $R_3''$ is a cyanoalkyl, hydroxyalkyl, carbalkoxy-alkyl, N,N-dialkylcarbamyl, N-alkylcarbamyl-alkyl or N,N-dialkylcarbamylalkyl group, are useful as diuretics and saluretics; some derivatives possess secretolytic activity.

2 Claims, No Drawings

NOVEL 2-AMINO METHYL-4,6-DIHALOGENPHENOL DERIVATIVES AND METHODS FOR THE PREPARATION THEREOF

CROSS-REFERENCE TO RELATED APPLICATION

This application is a continuation-in-part of copending application Ser. No. 429,984, filed Jan. 2, 1974, of Ludwig H. Schlager, entitled NOVEL 2-AMINOMETHYL-4,6-DIHALOGENPHENOL DERIVATIVES AND METHODS FOR THE PREPARATION THEREOF.

BACKGROUND OF THE INVENTION

1. Field of the Invention

The invention relates to novel 2-aminomethyl-4,6-dihalogenphenol derivatives and a method for preparing the same.

2. Description of the Prior Art

Principally an aminomethylation of halogen phenols is known (Journ.Am.Chem.Soc 74, 1518 (1952)). With respect to 2,4-dihalogen phenols also as amidomethylation, that means a "Tscherniac-Einhorn" reaction is described (see German Published Application No. 2,163,911).

SUMMARY OF THE INVENTION

According to the invention, there is provided a class of novel 2-aminomethyl-4,6-dihalogen-phenol derivatives and salts thereof with physiologically acceptable acids or bases having the formula:

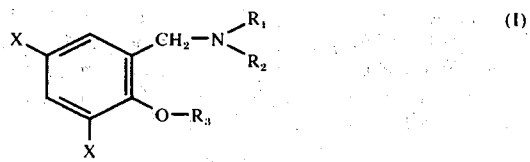

(I)

wherein X is the same halogen in both positions, $R_1$ is a hydrogen atom or a lower alkyl group, $R_2$ is an alkyl, cycloalkyl, aryl or aralkyl group, or $R_1$ and $R_2$ together with the nitrogen atom may form a saturated heterocyclic ring, which ring may be interrupted by an oxygen, nitrogen or sulfur atom, and $R_3$ is a hydrogen atom, an alkyl, alkoxyalkyl, carboxyalkyl, carbamylalkyl, aralkyl, acyl or sulfonyl group or a base radical, e.g. an alkali metal atom.

The invention also provides a method for preparing these compounds.

According to the invention the novel compounds are prepared by a method which comprises reacting a 2,4-dihalogenphenol of the formula:

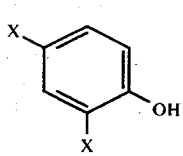

(II)

wherein X is as defined above with formaldehyde and an amine of the formula:

(III)

wherein $R_1$ and $R_2$ are as defined above, preferably in an inert solvent, and either converting the obtained 2-aminomethyl-4,6-dihalogenphenol of the formula:

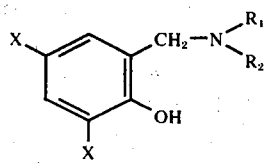

(IV)

wherein X, $R_1$ and $R_2$ are as defined above immediately in its salts with physiologically acceptable acids or bases or synthesizing the corresponding O-substituted derivatives of formula (I) by further reacting the free phenolic component (IV) or its alkali phenolate resp. with a compound of the formula:

$$Y - R_3' \qquad (V)$$

wherein $R_3'$ has the same meaning like $R_3$ with exception of hydrogen or base radical and Y is a reactive group, preferably a halogen atom, and optionally converting said O-substituted derivatives in a salt thereof.

According to the invention there is provided also a class of novel 2-aminomethyl-4,6-dihalogen-phenol derivatives and salts thereof with physiologically acceptable acids having the formula:

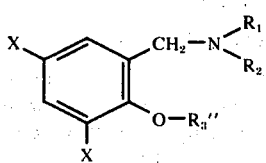

(I')

wherein X, $R_1$ and $R_2$ are as defined above and $R_3''$ may be a cyanoalkyl, hydroxyalkyl, carbalkoxyalkyl, N,N-dialkylcarbamyl, N-alkylcarbamyl-alkyl or N,N-dialkylcarbamyl-alkyl group.

According to the invention, the novel compounds of formula (I') are prepared by a method which comprises reacting compounds of formula (I), wherein $R_3$ is a hydrogen atom or a base radical (e.g. alkali) with compounds of the formula:

$$Y - R_3'' \qquad (V'')$$

wherein $R_3''$ is as defined above and Y is a reactive group, preferably a halogen atom.

It is advantageous to carry out the reactions as described below in aprotic solvents, e.g. hexamethylphosphoric acid triamide, under mild conditions (room temperature up to about 60° C). Thus, good yields are obtained. A possible competitive reaction of a quaternisation of the group

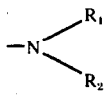

practically does not occur with the reaction conditions of the invention.

The compounds according to the invention (I) and (I') have pharmaceutically useful properties. The hydrochlorides thereof dissolve mostly easily in water and also in chloroform, so that said compounds have balanced hydrophilic and lipophilic properties. Especially those derivatives carrying a N,N-dialkylcarbamyl-alkyl group in the position of $R_3''$ show highly diuretic and saluretic activity; some of the derivatives also possess a secretolytic activity.

DESCRIPTION OF THE PREFERRED EMBODIMENTS

The following examples describe the preparation of the present compounds using the methods of the invention without, however, limiting the scope of the invention thereto.

EXAMPLE 1

453 g of N-methylcyclohexylamine are dropped to a mixture of 300 ml of formaldehyde (35%) and 2 l dioxane, cooled to 10° C, with stirring. Then 1008 g of dibromophenol are added to the mixture. The obtained mixture is heated for 3 hours under reflux and then evaporated in vacuo, until a syrupy consistence is obtained. By diluting the brown syrup with methanol and scratching the cooled solution crystalline N-(2-hydroxy-3,5-dibromobenzyl)-N-methylcyclohexylamine, m.p. 65°–67° C, is obtained, which is washed with methanol on a filter.

The hydrochloride of this compound is obtained from the mother liquor after adding alcoholic HCl-solution. After recrystallization from ethanol the hydrochloride melts at 182°–186° C.

EXAMPLE 2

6,08 g of lithium amide are added in portions to a solution of 100 g of the base obtained according to Example 1 in 150 ml of dimethylformamide with stirring. The temperature of the mixture rises to 40° C. Soon a colorless powder precipitates from the clear solution, which is the lithium phenolate of the used compound, m.p. 130° C.

EXAMPLE 3

105 ml of a solution of 29% sodium methylate are dropped to a solution of 200 g of the base obtained according to Example 1 in 600 ml of acetone with stirring. Then the solution is evaporated in vacuo and the remainder is stirred with ether, thereby crystallizing the sodium phenolate of the used compound, m.p. 200°–203° C.

EXAMPLE 4

A solution of 8,6 g of acetylchloride in 20 ml chloroform is dropped into a stirred solution of 37,7 g of the base obtained according to Example 1 in 100 ml chloroform. The temperature of the mixture rises to 40° C thereby. Then the mixture is heated for 30 minutes with reflux, the cooled solution is extracted with water, dried over $Na_2SO_4$ and evaporated in vacuo. The remainder is taken up in a small amount of isopropanol. By adding alcoholic HCl and ether to this solution the hydrochloride of N-(2-acetoxy-3,5-dibromobenzyl)-N-methylcyclohexylamine precipitates, melting after recrystallization from ethanol at 188°–192° C.

EXAMPLE 5

7,66 g of the lithium phenolate obtained according to Example 2 are dissolved in 300 ml of dimethylformamide. A solution of 3,43 g of ethyl iodide in 10 ml of dimethylformamide is dropped thereto with stirring. After 2 hours the reaction mixture is heated to 50° C and maintained for 1 hour at this temperature. Then the solvent is evaporated in vacuo. The remainder is taken up in chloroform, extracted with water and the dried chloroform solution is evaporated. Treating the remainder with alcoholic HCl solution gives the crystalline hydrochloride of N-(2-ethoxy-3,5-dibromobenzyl)-N-methylcyclohexylamine, melting at 205° C after recrystallization from ethanol.

EXAMPLE 6

A mixture of 95 ml of 35% formaldehyde solution and 100 ml of dioxane is dropped into a solution of 80 g of tertiary butylamine in 350 ml of dioxane, cooled to 15° C, with stirring. The mixture is allowed to stand over night, then heated to 80° C. In the course of 4 hours a solution of 252 g of 2,4-dibromophenol in 250 ml of dioxane is dropped thereto, precipitating thereby the main charge of the reaction product. 1 hour after completion of this addition it is cooled, the precipitate is sucked off, washed with ethanol on the filter and dried. By concentrating the dioxane-mother liquor and the alcoholic washing liquid further material is obtained. Remaining reaction product precipitates from the dioxane concentrate in form of the hydrochloride by heating with alcoholic HCl. The hydrochloride is converted in $H_2O/CHCl_3$ in the free base with $NaHCO_3$. Total yield = 268 g (79,5% of the theory). Recrystallization from acetic ester yields the N-(2-hydroxy-3,5-dibromobenzyl)-tert.butylamine in form of colorless felted needles, melting at 173°–175° C.

EXAMPLE 7

4 ml of sodium methylate solution (29%) are dropped to a suspension of 6,74 g of the base obtained according to Example 6 in 10 ml of hexamethylphosphoric acid triamide ("HMPT") with stirring. Thus, a yellowish solution is obtained. Said solution is heated to 40° C. In the course of 3 hours a solution of 3 g of benzylchloride in 5 ml of HMPT is dropped thereto. The stirring is continued 3 hours at a temperature of 40° C. Then the cooled mixture is added to 200 ml of an icecold aqueous NaCl solution and extracted with ether several times. The combined ether extracts are extracted with 0,1N NaOH and then with $H_2O$, dried over $Na_2SO_4$, stirred with charcoal and filtered. By adding alcoholic HCl to the filtrate the hydrochloride of N-(2-benzyloxy-3,5-dibromobenzyl)-tert.butylamine precipitates. It is recrystallized from ethanol und melts at 204°–208° C. Yield = 7,9 g (85,4% of the theory).

In analogy to the methods described in the above Examples further derivatives of formula (I) are obtained. They are summarized in the following Table 1.

Table 1

| | m.p. ° C | m.p. ° C |
| --- | --- | --- |

Table 1-continued

| X | $R_1$ | $R_2$ | $R_3$ | free base | hydrochloride |
|---|---|---|---|---|---|
| Br | $CH_3$ | cyclohexyl | $CO.CH_2.C_6H_5$ | | 153 – 157 |
| Br | $CH_3$ | cyclohexyl | $SO_2.C_6H_4.CH_3(p)$ | 94 – 96 | |
| Br | $CH_3$ | cyclohexyl | $SO_2.CH_3$ | | 198 – 203 |
| Br | $CH_3$ | cyclohexyl | $CO.CH_2.O.CO.CH_3$ | | 161 – 168 |
| Br | $CH_3$ | cyclohexyl | $CH_2.C_6H_5$ | | 131 – 134 |
| Br | $CH_3$ | cyclohexyl | $CH_3$ | | 185 – 192 |
| Br | $CH_3$ | cyclohexyl | $(CH_2)_2.O.C_2H_5$ | | 142 – 144 |
| Br | $CH_3$ | cyclohexyl | $CH_2.CO.NH_2$ | 127 – 128 | |
| Br | $CH_3$ | cyclohexyl | $CH_2COOH$ | | 178 – 184 |
| Br | $CH_3$ | cyclohexyl | $CH_2.C_6H_4.Cl(o)$ | | 132 – 135 |
| Br | $CH_3$ | cyclohexyl | $CH_2.C_6H_4.Cl(p)$ | | 165 – 167 |
| Cl | $CH_3$ | cyclohexyl | H | 55 – 57 (Na-salt: m.p. 170 – 175° C) | 182 – 184 |
| Cl | $CH_3$ | cyclohexyl | $CH_2COOH$ | | 176 – 186 |
| Cl | $CH_3$ | cyclohexyl | $COCH_3$ | | 182 – 188 |
| Cl | $CH_3$ | cyclohexyl | $CO.CH_2.C_6H_5$ | | 144 – 150 |
| Cl | $CH_3$ | cyclohexyl | $CH_2.C_6H_5$ | | 163 – 167 |

| X | $-N\langle{R_1 \atop R_2}$ | $R_3$ | m.p. °C free base | m.p. °C hydrochloride |
|---|---|---|---|---|
| Br | —N(morpholino) | H | 85 – 87 (Na-salt: m.p. 228–231° C) | 185 – 191 |
| Br | —N(morpholino) | $COCH_3$ | | 193 – 199 |
| Br | —N(morpholino) | $CH_2.C_6H_5$ | | 184,5–186,5 |
| Br | —N(morpholino) | $CH_2.C_6H_4.Cl(o)$ | | 188 – 195 |
| Br | —N(N-methylpiperazino) | H | 104 (Na-salt: m.p. >300° C) | dihydrochloride 212 – 216 |
| Br | —N(N-methylpiperazino) | $COCH_3$ | | 201 – 208 |
| Br | —N(N-methylpiperazino) | $CH_2C_6H_5$ | 127 – 130 | 189 – 196 |
| Br | —N(N-hydroxyethylpiperazino) | H | 98 – 104 (Na-salt: m.p. 246–249° C) | |
| Br | —N(N-hydroxyethylpiperazino) | $CH_2.C_6H_4Cl(o)$ | | 179 – 183 |
| Br | —N(piperidino) | H | 100 – 101 (Na-salt: m.p. 250–255° C) | |
| Br | —N(piperidino) | $CH_2.C_6H_5$ | | 176 – 179 |

EXAMPLE 8

A solution of 6,4 g of chloroacetic acid dimethylamide in 10 ml of HMPT is dropped to a suspension of 20 g of the sodium salt of N-(2-hydroxy-3,5-dibromobenzyl)-N-methylcyclohexylamine in 20 ml of hexamethylphosphoric acid triamide (HMPT) for 3 hours at 40° C with stirring. The reaction is continued for 1 hour at 40° C. Then the mixture is cooled and stirred with 250 ml of an icecold saturated aqueous saline solution. The syrupy mass precipitated thereby is dissolved in diethyl ether (after decanting the aqueous phase), the solution is extracted with diluted NaOH and then with water, dried over $Na_2SO_4$ and after filtration alcoholic HCl solution is added. Thus, a syrupy hydrochloride is precipitated, which crystallizes after decanting the ether solution by boiling with CCl₄. The hydrochloride of N-[2-(N',N-dimethylcarbamylmethoxy)-3,5-dibromobenzyl]-N-methyl-cyclohexylamine melts at 107°–113° C after recrystallization from acetone/CCl₄. After recrystallization from acetone-ether the melting point rises to 132°–136° C.

EXAMPLE 9

7,5 g of chloroacetonitrile are dropped to a suspension of 20 g of the sodium salt of N-(2-hydroxy-3,5-dibromobenzyl)-N-methyl-cyclohexylamine in 30 ml of HMPT at room temperature with stirring. After 5 hours the reaction mixture is stirred with 250 ml of icecold saturated aqueous saline. The aqueous phase is decanted from the precipitated product, the latter is taken up with CHCl₃. The chloroform solution is dried over Na₂SO₄, filtered and evaporated. By adding alcoholic HCl solution to the remainder and diluting with acetone the hydrochloride of N-(2-cyanomethoxy-3,5-dibromobenzyl)-N-methylcyclohexylamine is precipitated. This product is recrystallized from isopropanol and melts then at 186°–189° C.

According to the methods of Examples 8 and 9 further derivatives are obtained, which are summarized in the following Table 2.

Table 2

| X | R₁ | R₂ | R₃ | m.p. °C hydrochloride |
|---|----|----|----|----------------------|
| Br | CH₃ | cyclohexyl | CH₂COOC₂H₅ | 138–145 |
| Br | CH₃ | cyclohexyl | CH₂CH₂ . OH | 160–166 |
| Br | CH₃ | cyclohexyl | CH₂CO . N(C₂H₅)₂ | 152–157 |
| Br | CH₃ | cyclohexyl | CO . N(C₂H₅)₂ | 175–185 |
| Cl | CH₃ | cyclohexyl | CH₂COOC₂H₅ | 143–146 |
| Cl | CH₃ | cyclohexyl | CH₂CO . N(C₂H₅)₂ | 150–153 |

| X | −N<R₁,R₂ | R₃ | m.p. °C hydrochloride |
|---|----------|----|-----------------------|
| Br | −N(morpholino) | CH₂COOC₂H₅ | 150–157 |
| Br | −N(piperazino)N−CH₂CH₂OH | CH₂COOC₂H₅ | 183–187 |
| Br | −NH−C(CH₃)₃ | CH₂CO . N(C₂H₅)₂ | 171–174 |
| Br | −NH−cyclohexyl | CH₂CO . N(C₂H₅)₂ | 180–183 |

EXAMPLE 10

182.6 gms of N-(2-hydroxy-3,5-dibromobenzyl)-tert.butylamine are suspended in 360 mls of fresh distilled dimethylformamide. 16.3 gms of NaH (80% in oil) are added in small portions, thereby the resulting greenish-yellow solution warming to about 55° C. It is stirred further 30 minutes with exclusion of moisture, whereafter 81.5 gms of chloroacetic acid diethylamide are added within 7 hours at 45° C. After cooling it is sucked off and the filtrate is evaporated in vacuo up to syrupy consistence. The red-brown syrup is stirred with water several times, taken up into isopropylether and extracted with 2N NaOH. After extracting again the aqueous phases with isopropyl ether the combined isopropyl ether solutions are dried over anhydrous Na₂SO₄, treated with charcoal and filtered. By adding alcoholic HCl the hydrochloride of N-[2-(N',N''-diethyl-carbamyl-methoxy)-3,5-dibromobenzyl]-tertiary butylamine precipitates from the filtrate in muddy form. It crystallizes after cooling and triturating and melts after recrystallization from ethanol/ether at 171°–174° C.

EXAMPLE 11

To a solution of 198.4 gms of cyclohexylamine in 1 liter of dioxane cooled to 15° C., 174 mls of aqueous formaldehyde solution (35%) are dropped with stirring. Then a solution of 503.8 gms of 2,4-dibromophenol in 1 liter of dioxane is added and heated with reflux for 10 hours. The product crystallized by cooling overnight is sucked off, washed on the filter with ethanol and recrystallized from ethanol. The dried N-(2-hydroxy-3,5-dibromo-benzyl)-cyclohexylamine melts at 168°–171° C. Further crude product is obtained by evaporating the combined filtrates.

To a suspension of 36.3 gms of the pure N-(2-hydroxy-3,5-dibromo-benzyl)-cyclohexylamine in 50 mls of HMPT 18.7 mls of a 29% sodium methylate solution are dropped with stirring. Then a solution of 16.5 gms of chloroacetic acid diethylamide in 20 mls of HMPT is dropped thereto at 40° C within 4 hours. The cooled mixture is treated with 500 mls of ice-water. The oil separated thereby is taken up into ether, the etheric solution is extracted with 2N NaOH and with H₂O, dried over anhydrous Na₂SO₄ and filter after treatment with charcoal. By adding the etheric filtrate with alcoholic HCl the hydrochloride of N-[2-(N',N'-diethylcarbamylmethoxy)-3,5-dibromo-benzyl]-cyclohexylamine is precipitated; after recrystallization from ethanol/ether the melting point is 180°–183° C.

Examples 10 and 11 are methods to produce the last two compounds of Table 2.

The compounds of Examples 10 and 11 have diuretic and saluretic activity, but not a secretolytic activity.

EXAMPLE 12

Chemistry and pharmacological activity of the compound of Example 10.

1. Chemistry

Se 852.HCl is the hydrochloride of N-[2-(N',N'-diathylcarbamylmethoxy-)-3,5-dibromobenzyl]-tert.butylamine having the following formula:

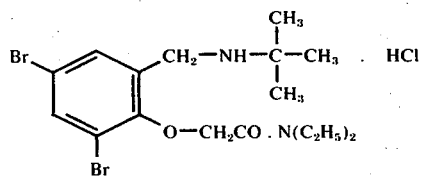

It is a white, bitter tasting powder which is soluble in water and has a fusion point of 171°–174° C.

2. Toxicities 2.1 single dose:
  DL₅₀ = 44 mg/kg, i.v., Mouse
  DL₅₀ = 344 mg/kg orally, Mouse
  DL₅₀ = 480 mg/kg; orally, Male rat
2.2 Repeated dose (Short term toxicity according to LIM et al.)

$DL_{50} = 535$ mg/kg; orally, male rat.

3. Diuresis and Saluresis
3.1 Method:
That of Kagawa and Kalm (modified).
3.2 Results:
See Table 3.

4. Heart — Circulation
4.1 Method:
Blood pressure taken from the A. Carotis (female rat, ethylurethane-narcosis). Heart frequency, EKG using an EKA pulse device. Respiration using a magnetic pulse meter.

4.2 RESULTS
4.2.1.1. Blood pressure after i.v. application:
1 mg/kg - no effect,
2–10 mg/kg abrupt drop by 30–50% with subsequent slight increase of 5%.
4.2.1.2 Blood pressure after oral application:
5–60 mg/kg no effect.
80 mg/kg increase of up to 15%.
4.2.2. Heart frequency:
With i.v. and oral application, frequency reduction of 5% for 2–3 hours.
4.2.3. EKG:
No changes.
4.2.4. Respiration
4.2.4.1.i.v. application:
1–5 mg/kg no change
10 mg/kg frequency reduction of up to 15%.
4.2.4.2. oral application
20–80 mg/kg frequency reduction of up to 10%.

5. Effect on Isolated Organs
5.1 Magnus method
5.2 Results:
Measured against Carbaminoylchloinchloride.
Spasmolytic effect.
$DE_{50} = 6,3 \cdot 10^{-4}$ g/ml

6. Influence on the Blood Sugar
6.1 Method: Toluidine method.
6.2 Results:
10 mg/kg produced no change in the blood sugar.

7. Influence on Gastric Secretion
Method:
The pylorus was loosened (removed) one hour after the oral dose and after a further 3 hours the quantity of stomach acid was determined by titration.
7.2 Results:
10 mg/kg — Increase of 23% in the stomach acid.
20 mg/kg — Increase of 29% in the stomach acid.

8. Influence on Spontaneous Motility
8.1 Method:
"Animex" measuring device.
8.2 Results:
15 mg/kg — reduction of 13%.

9. Protein Union
9.1 Method:
50 or 25 mg Se 852. HCl were dissolved on each occasion in 10 ml distilled water or in a 10 ml fresh human plasma pool heated to 37° C. The human plasma was then incubated for 15 minutes at 37° C and thereafter centrifuged for 18 hours at 4° C with 380.000 × g. The clear supernatant liquids were siphoned off and each 5 ml of the supernatant liquid or of the corresponding comparison solution rendered alkaline with 2 drops of 0.1 n NaOH and shaken 3 times with 10 ml ether. The ether extracts were dried with sodium sulfate. These extracts were then evaporated to dryness in a rotary evaporator at 40° C. The residues were dissolved in 2 ml ether and 0.05 ml of this ethereal solution was applied to a thin layer plate (silica gel G, layer thickness 0.25). Disengagement was obtained with Methanol (distance 10 cms). The bases were then localized by spraying with iodine platinate solution and scraped from the plate. Extraction was effected by shaking for 1 minute with 4 ml 1% acetic acid in methanol. After centrifuging, the extracted materials were photometrically evaluated in comparison with a blank value of the plate of 200 – 300 nm The percentage of free concentrations of active material in the plasma was calculated from the quotients of the extinction maxima of the comparison solutions and the ultra-centrifuged plasma solutions.
9.2 Results:
The average value of three figures was:

10. Changes in the Urea, sGOT and γGT contents
10.1 Method:
The tests were carried out with albino rats (Sprague Dawley) weighing 250–270 g. 2,4,6,12,24,48 and 72 hours after oral administration of the preparation, measurements were effected on the serum of the animals. 3 rats were used each time measurements were effected. A corresponding number of untreated animals were used for control purposes.
10.2 Results:
In these tests we were unable to determine any significant changes in the urea, sGOT and γGT values after doses of Se 852.HCl amounting to 40 mg/kg or 20 mg/kg body weight.

TABLE 3

DIURESIS AND SALURESIS TEST
Comparison of Furosemid and Se 852 . HCl

| Substance | Dosage mg/kg per bone | Urea volumes collected in 6 hrs. per kg. rat (in ml). | $NA^{(r)}$ | $K^{(r)}$ | $Cl^{(r)}$ | Na/K |
|---|---|---|---|---|---|---|
| Se 852 . HCl | 10,0 | 27,83 | 0,634 | 0,450 | 0,654 | 1,409 |
| Furosemid | 10,0 | 19,69 | 0,597 | 0,467 | 0,687 | 1,278 |
| Se 852 . HCl | 20,0 | 32,93 | 0,932 | 0,659 | 0,640 | 1,414 |
| Furosemid | 20,0 | 24,05 | 0,910 | 0,603 | 1,260 | 1,509 |
| Se 852 . HCl | 40,0 | 48,69 | 2,050 | 1,687 | 2,069 | 1,215 |
| Furosemid | 40,0 | 45,55 | 3,337 | 1,375 | 4,584 | 2,427 |
| Se 852 . HCl | 60,0 | 57,74 | 3,004 | 2,397 | 3,610 | 1,253 |
| Furosemid | 60,0 | 46,69 | 3,339 | 1,367 | 5,316 | 2,443 |

TABLE 3-continued

DIURESIS AND SALURESIS TEST
Comparison of Furosemid and Se 852 . HCl

| Substance | Dosage mg/kg per bone | Urea volumes collected in 6 hrs. per kg. rat (in ml). | NA(x) | K(x) | Cl(x) | Na/K |
|---|---|---|---|---|---|---|
| Control Animals | — | 18,81 | 0,337 | 0,338 | 0,223 | 0,997 |

(x)Expressed in "milli" equivalents per kg. rat

Having thus described my invention, what I desire to secure by Letters Patent and hereby claim is:

1. N-[2-(N',N'-diethyl-carbamyl-methoxy)-3,5-dibromobenzyl]-tertiary butylamine.

2. N-[2-(N',N'-diethyl carbamyl-methoxy)-3,5-dibromobenzyl] cyclohexylamine.

* * * * *